(12) United States Patent
Burgoa Roman et al.

(10) Patent No.: US 9,171,362 B2
(45) Date of Patent: *Oct. 27, 2015

(54) METHOD FOR DETERMINING THE LUMINANCE OF TRAFFIC SIGNS AND DEVICE FOR IMPLEMENTING SAME

(71) Applicant: DBI/CIDAUT Technologies, LLC, Hazelton, PA (US)

(72) Inventors: Francisco Javier Burgoa Roman, Boecillo (ES); Jose Antonio Gutierrez Mendez, Boecillo (ES); Alberto Mansilla Gallo, Boecillo (ES); Diego Ortiz de Lejarazu Machin, Boecillo (ES); Alberto Senen Perales Garcia, Boecillo (ES)

(73) Assignee: DBI/Cidaut Technologies, LLC, Hazelton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/265,747

(22) Filed: Apr. 30, 2014

(65) Prior Publication Data

US 2014/0233850 A1 Aug. 21, 2014

Related U.S. Application Data

(63) Continuation of application No. 12/866,888, filed as application No. PCT/ES2008/000214 on Apr. 8, 2008.

(30) Foreign Application Priority Data

Feb. 12, 2008 (ES) .................. P200800371

(51) Int. Cl.
*G06T 5/50* (2006.01)
*B60Q 1/08* (2006.01)
(Continued)

(52) U.S. Cl.
CPC . *G06T 5/50* (2013.01); *B60Q 1/085* (2013.01); *B60Q 1/18* (2013.01); *G01N 21/55* (2013.01); *B60Q 2300/314* (2013.01); *B60Q 2300/45* (2013.01); *G01N 2021/551* (2013.01)

(58) Field of Classification Search
CPC . G01N 21/55; G01N 2021/551; B60Q 1/085; B60Q 2300/45; B60Q 1/18; B60Q 2300/314; B60Q 1/2603; B60R 2300/103; B60R 21/01538; G06T 5/50

USPC ................. 382/100, 103, 104, 190, 274, 275; 348/148

See application file for complete search history.

(56) References Cited

U.S. PATENT DOCUMENTS

| 4,553,848 | A | 11/1985 | Rosicke et al. |
| 6,266,442 | B1 | 7/2001 | Laumeyer et al. |

(Continued)

FOREIGN PATENT DOCUMENTS

| EP | 1486799 | 12/2004 | |
| EP | 1486799 A2 * | 12/2004 | .............. G01S 17/89 |

(Continued)

OTHER PUBLICATIONS

International Patent Application No. PCT/ES2008/000214, International Search Report, dated Oct. 28, 2008, 8 pages.
(Continued)

*Primary Examiner* — Michael Vanchy, Jr.
(74) *Attorney, Agent, or Firm* — Morgan Lewis & Bockius LLP

(57) ABSTRACT

The method of the invention comprises: obtaining a sequence of at least two images, with different levels of illumination; extracting the region containing the sign in the image; calculating the luminance values of the signs; and obtaining the difference in luminance of the sign corresponding to the two levels of illumination. The value obtained is the luminance of the sign (11) corresponding to an illumination equal to the difference between the illuminations, or additional illumination. This result is based on the additive property of luminance, according to which the luminance of a sign is the sum of the luminance produced by each source of illumination. A basic illumination device (5), an additional illumination device (7), at least one camera for taking images, and image recording, positioning and synchronism systems are required to implement the method.

47 Claims, 2 Drawing Sheets

(51) Int. Cl.
*B60Q 1/18* (2006.01)
*G01N 21/55* (2014.01)

(56) References Cited

U.S. PATENT DOCUMENTS

| | | |
|---|---|---|
| 6,674,878 B2 | 1/2004 | Retterath et al. |
| 6,891,960 B2 | 5/2005 | Retterath et al. |
| 7,043,057 B2 | 5/2006 | Retterath et al. |
| 7,173,707 B2 | 2/2007 | Retterath et al. |
| 7,298,487 B2 | 11/2007 | Hansen et al. |
| 7,411,681 B2 | 8/2008 | Retterath et al. |
| 7,515,736 B2 | 4/2009 | Retterath et al. |
| 7,995,796 B2 | 8/2011 | Retterath et al. |
| 2002/0176605 A1* | 11/2002 | Stafsudd et al. ............ 382/106 |
| 2005/0146725 A1 | 7/2005 | Hansen et al. |
| 2007/0216904 A1 | 9/2007 | Retterath et al. |
| 2007/0262765 A1* | 11/2007 | Joos et al. ................. 323/299 |
| 2010/0316252 A1 | 12/2010 | Roman et al. |
| 2012/0065940 A1 | 3/2012 | Retterath et al. |
| 2013/0271613 A1 | 10/2013 | Retterath et al. |

FOREIGN PATENT DOCUMENTS

| | | |
|---|---|---|
| EP | 1580074 | 9/2005 |
| EP | 1976296 | 1/2008 |
| FR | 2661248 | 10/1991 |
| JP | 2000149195 | 5/2000 |
| JP | 2000353292 | 12/2000 |
| JP | 2008015970 | 1/2008 |
| TW | 242637 | 11/2005 |
| WO | 2007/083741 | 7/2007 |

OTHER PUBLICATIONS

International Patent Application No. PCT/ES2008/000214, Written Opinion of the International Searching Authority, dated Oct. 28, 2008, 17 pages.
European Patent Application No. 08761461, Response to Communication Pursuant to 161 (2) and 162 EP, dated Oct. 19, 2010, 6 pages.
European Patent Application No. 08761461, Supplementary European Search Report and Opinion, dated May 23, 2011, 7 pages.
European Patent Application No. 08761461., Response to European Search Report and Opinion, dated Oct. 20, 2011, 13 pages.
European Patent Application No. 08761461, Communication Pursuant to Article 94(3) EPC, dated Dec. 18, 2012, 6 pages.
European Patent Application No. 08761461, Response to Communication Pursuant to Article 94(3) EPC, dated Mar. 26, 2013, 14 pages.
European Patent Application No. 08761461, Corrected Form 1703, dated Oct. 11, 2011, 6 pages.

* cited by examiner

METHOD FOR DETERMINING THE LUMINANCE OF TRAFFIC SIGNS AND DEVICE FOR IMPLEMENTING SAME

CROSS REFERENCE TO APPLICATIONS

This application is a continuation of U.S. patent application Ser. No. 12/866,888 filed Aug. 9, 2010 which is a U.S. National Stage Patent Application of International Application No. PCT/ES2008/000214, filed Apr. 8, 2008, which claims priority to Spanish Application No.: P200800371 filed Feb. 12, 2008 all of which are incorporated herein by reference in their entireties.

The present invention relates to a procedure and device permitting the luminance provided by a sign installed on the road to be calculated, isolating the existing ambient illumination conditions. The calculation of the luminance is carried out on the basis of analysing the images gathered by an image recording system, and is applied to all signs appearing in those images.

The present invention encompasses the calculation of the luminance both of signs consisting of back-reflecting material and those that are internally lit, and to any traffic sign in general.

The invention comprises a set of lights and a procedure permitting the elimination of any effects which external illumination could have on the measurement, whether these come from other road users or from ambient illumination, along with a control system for the illumination provided by the vehicle. The illumination system used by the invention complies with existing standards in terms of illumination systems fitted to vehicles, the intensity is not high and it is not disturbing to road users, and the tests can be conducted without interrupting the traffic.

The invention comprises a moving system for the synchronized recording of images and data, referenced by means of a positioning system and an automatic system for sign identification and processing.

BACKGROUND OF THE INVENTION

The evaluation of the state of traffic signs installed on the road has normally been done by means of analysing two parameters:

The back-reflection coefficient: Property of back-reflecting materials. which permits light to be returned in the same direction as the incident light.

The luminance: Quantity of light returned by the sign to which the eye is sensitive.

The back-reflection coefficient is a parameter characteristic of the material, whose value falls off as the sign deteriorates. In order to evaluate it, systems have been developed such as those described in documents U.S. Pat. No. 7,173,707, U.S. Pat. No. 7,043,057 and U.S. Pat. No. 6,674,878, in which procedures are described for measuring the multiple back-reflection values or three-dimensional map of back-reflection coefficients provided by the sign. This measurement is made via a system that is capable of providing illumination by means of a high intensity stroboscopic light and which measures the different values of light intensity. It then generates some surfaces of back-reflection coefficients and simulates the back-reflection values along the road, recreating a virtual drive.

But, although the back-reflection coefficient or the three-dimensional map of back-reflection coefficients is a characteristic parameter of the sign, in order to obtain the luminance value (the parameter that really defines the visibility conditions) indirect methods have to be applied in which theoretical models of the illumination are used. The stated documents therefore lead to the problem of how to make a direct measurement of the luminance without having to be subject to intermediate operations based on unreal theoretical models.

Another problem that is raised by using the back-reflection coefficient lies in the fact that it is only applicable to back-reflecting signs, and signs that are internally lit have to be discarded from the analysis.

To make a direct calculation of the luminance (in units of $cd/m^2$) there exist various apparatus known as luminance meters. In order to make a measurement of the magnitude, these devices require certain specific conditions of stability and illumination, and the measurement they provide is of a point source. This equipment therefore displays serious drawbacks for making a simultaneous measurement while moving of all the signs lying within the analysis zone. The luminance measurements would have to be made one at a time, and in different zones of the sign, in order to then obtain an average of them.

Moreover, as the measurement requires a strictly controlled type of illumination, we would have to discard data that is influenced by the effects of moving traffic, external lighting, etc.

As a consequence, it is an objective of the present invention to have a procedure and a device that would permit the luminance of the sign to be determined:

Directly, making a direct measurement of the physical parameter.
Automatically, for all signs appearing in a scene.
While circulating with a vehicle.
On the basis of a known or standardized light source, independently of the existence of other external light sources at the moment of the measurement.
Independently of whether the sign is back-reflecting, or internally lit, or any other kind of traffic sign.
Independently of the level of back-reflection which this type of sign provides once installed on the road.

DESCRIPTION OF THE INVENTION

The present invention comprises a procedure and device for calculating the luminance provided by traffic signs arranged along the road, the measurement being based on certain light sources whose illumination conditions are known and controlled in turns of form and intensity. To achieve this, the images picked up by a mobile data gathering system are used. The procedure permits the interferences produced by uncontrolled external illuminations to be cancelled out, obtaining the luminance in the zones that are sought. The internal oscillations of the vehicle affecting its own illumination are also cancelled out. The invention permits simultaneous analysis of all the signs appearing in the images gathered by the moving vehicle, and is applied both to the back-reflecting type and to internally lit signs or to any other kind of traffic sign.

The present invention provides a series of improvements over existing systems by permitting a direct calculation to be made of the luminance from a moving vehicle, without any need to use theoretical models of illumination. It isolates the measurement from the interferences produced by light sources other than those of the vehicle. It also allows measurements to be carried out safely, without any need to cut off the traffic, since it does not use high intensity lamps and the measurements can be made at the usual road speed.

The visibility of a vertical road sign is directly related to the luminance provided by that sign. Luminance is defined as the ratio of luminous intensity of the surface apparently seen by the eye in a defined direction. Its unit is cd/m².

With the procedure described in the present invention, a measurement is made of the luminance using at least one digital camera, irrespective of whether it is colour or black and white, duly calibrated, in such a way that the luminous energy in the form of photons received by each pixel of the camera sensor is reflected as the luminance of a section of material. The camera or cameras to be used can be digital, analogue or any other kind, with their corresponding accessories for carrying out those operations.

In order to obtain the luminance level of each pixel in the image starting from a colour or black and white camera, it is necessary to perform two transformations. First of all, in the case of colour cameras, each level of red, blue and green of the pixel is combined with some appropriate weightings, specified in standard CIE—121, in order to convert it to a grey level. Secondly, it is transformed directly to luminance starting from a change equation obtained by comparison with a laboratory luminance meter.

With the method described, by using at least one digital camera it is possible to cover several signs simultaneously if they appear in the image. The images are processed in such a way that each sign is automatically identified and the luminance values are obtained for each of them.

The light intensity provided for the sign, whether this be from the actual vehicle itself or from other sources in the environs, has a direct influence on the measurement of the luminance of the back-reflecting materials. For the correct measurement, an illumination has been considered that eliminates the variability owing to the internal oscillations of the vehicle (of voltage, for example).

Moreover, in order to cancel out the perturbations produced by external light sources, a calculation technique of the luminance is proposed based on a differentiation of the values starting from at least two different illumination levels.

In some types of vertical signs, the luminance is provided by an internally generated illumination. On the other hand, in others it depends on the light provided by an external illumination and which is returned by the vertical sign, as occurs in the case of back-reflecting materials. The procedure and device proposed here are applicable to any traffic sign.

The procedure of the present invention for calculating the luminance comprises the following stages:

Obtaining a sequence of images composed of at least two images with different illumination levels.
Extracting the region where the sign is on the image.
Calculating the luminance values of the signs.
Obtaining the luminance difference of the sign corresponding to the two illumination levels.

The value obtained is the luminance of the sign corresponding to an illumination equal to the difference in the illuminations, or additional illumination. This result is based on the additive property of luminance, according to which the luminance calculated for each sign is the sum of the luminances produced by each light source.

In one of the images, the luminance is the sum of that due to the base illumination $L_a$, that due to the additional illumination $L_b$ and the uncontrolled ambient illumination $L_c$ (other vehicles, public lighting, etc). So the measured luminance is $$L1 = L_a - L_b + L_c,$$

Analogously, for the other image, the luminance will be due to the base illumination base $L_a$ and the ambient illumination $L_d$. The measured luminance will be:

$$L2 = L_a + L_d.$$

As the synchronism system ensures that the difference between the images to process is minimum in terms of the ambient illumination, we can assume that:

$$L_c = L_d.$$

If we deduct one level from the other, we obtain the value of the differential luminance corresponding to the additional illumination.

$$\Delta L = L1 - L2 = L_b$$

In this way a luminance value is obtained that is based on some lamps whose illumination conditions are known and controlled in terms of form and intensity, and which is independent of other uncontrolled external light sources.

In order to carry out the procedure of the invention, a device is used which, fitted to a vehicle, comprises:

At least one camera for capturing the images.
A base illumination device.
An additional illumination device.
A positioning system.
A system for image and data recording and treatment.
A synchronism system.

Among the advantages presented by the invention we can point out:

It is not based on point source measurements, like those that can be provided by back-reflectometers or luminance meters.
The analysis is carried out automatically for all the signs appearing in a scene.
The measurements are taken by means of a moving vehicle.
The measurement is made for a light source whose photometry is known and its level of light intensity is controlled.
The measurement is not affected by the existence of other eternal light sources, ambient or similar.
It permits an analysis of its state of visibility, independently of the level of back-reflection that the sign provides once installed on the road.
It functions independently of whether the sign is back-reflecting or internally lit, or any other kind.

BRIEF DESCRIPTION OF THE DRAWINGS

To complement the foregoing description, and with the aim of aiding a better understanding of the characteristics of the invention, a detailed description of a preferred embodiment is going to be made, on the basis of a set of plans accompanying this descriptive specification in which, on an orientative rather than limiting basis, the following has been represented.

FIG. 3 shows the vehicle with the base illumination and additional illumination switched on.
FIG. 4 shows the vehicle with just the base illumination switched on.

In the above figures, the numerical references correspond to the following parts and elements.

1. Driver.
2. Sign panel.
3. Distance between the driver and the sign.
4. Normal to the sign panel 2.
5. Base illumination.
6. Stabilizer for the base illumination.

7. Additional Illumination.
8. Adjustment and control of the additional illumination.
9. Light intensity sensor.
10. Public lighting.
11. Vertical traffic sign.

DETAILED DESCRIPTION OF A PREFERRED EMBODIMENT

Figure 1:
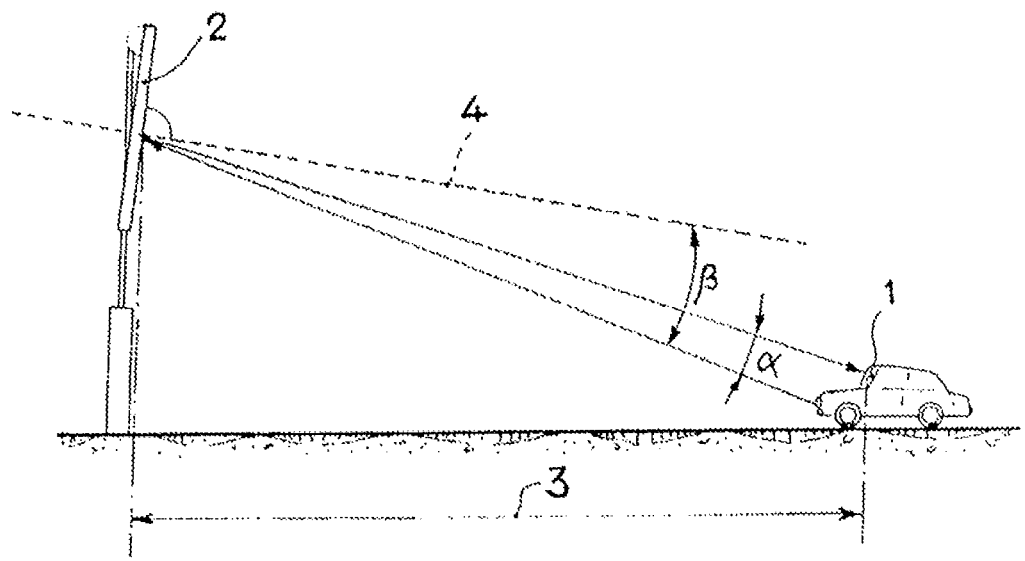
FIG. 1 shows a vehicle fitted with the device of the invention, approaching a traffic sign.

As can be seen in FIG. 1, a driver (1), as he goes along the road, perceives the information shown in the different signing elements. For a sign panel (2) lying within the angle of vision of the driver (1), at a distance (3) and in a defined instant, an angle of entrance β is defined formed between the light beam incident on the luminous surface at a point and normal (4) to that surface at that point, and also an angle of observation α formed by the light beam incident on the surface and the reflected light reaching the eyes of the driver (1). As the driver approaches the sign these angles change and the luminance perceived by the observer varies.

The luminance provided by a sign, especially if it consists of a back-reflecting material, depends on various factors:
  Contributed light. In case of internally lit signs, the reflected light is independent of the contributed light, but for back-reflecting materials, the greater the amount of light that is contributed to the sign, the more light that is reflected.
  Angle of entrance β and of observation α.
  Special properties of the material. In particular the variation in back-reflection with the angle of visualization with respect to the normal.
  The rotation of the sign about its axes (angles of twist, roll and dip).

In order to calculate the distance of the vehicle from the sign, a technique will be used based on the analysis of the images, using a single camera, though it can be extended to an array of cameras or specific techniques of triangulation or stereovision can be used. The procedure used in the present embodiment starts from the analysis of the image by known techniques of artificial vision which permits the position of an object of interest to be determined on that image on the basis of the size of that object as it appears in the image. Applied to different images of the same object, whose cadence is known thanks to the synchronism system, it is possible to establish a direct relation between the real size of the sign, the size of the sign in the image and the distance to the sign. Taking samples of the sizes of the object in the image, as well as the relative distances of the different images to one chosen as reference, it is possible to generate a set of geometric transformation equations on the basis of which the distance that is sought and the size of the object can be determined.

In order to carry out the procedure of the invention for determination of the luminance, a device is used which, fitted to a vehicle, comprises at least:
  One camera for capturing the images.
  A base illumination device.
  An additional illumination device.
  A positioning system.
  A system for image and data recording and treatment.
  A synchronism system.
Cameras The aim of the present invention is to study the luminance perceived by the driver. For this reason, the location has been considered of at least one of the cameras in a suitable position on the vehicle that is close to the eye of the driver.

Digital cameras permit the colour coordinates of objects to be represented in an image defined by a set of pixels.

The representation of the colour is normally done by means of the coordinates R, G, B (Red, Green, Blue) though there exist other systems, for example in 1931 the International Commission on Illumination established the system XYZ or CIE 1931. In it, the Y component represents the energy or luminance of the pixel and X and Z the colour. For standard camera systems (PAL, NTSC) many different combinations have been defined for transforming the RGB system to XYZ, as in the case of standard ITU.BT-601. In this way, in order to obtain the luminance of an object, it will suffice to carry out the transformation between the systems and determine the value of Y.

In the system used in this embodiment, and depending on the camera, a conversion will be applied like that described above (standard) or a non-standard transformation that comprises the following steps:
  A standard illuminant is selected defined by the CIE.
  A white balance is carried out (see document "Digital Color Imaging Handbook". Gaurav Sharma, ed. CRC PRESS, Boca Raton, N.Y., Washington, D.C.).
  Using a colour card according to the CIE 1931 standard, obtain the colour coordinates of pure red, green and blue with the camera.
  Using a colour card, obtain the XYZ colour coordinates of pure red, green and blue with a colorimeter as per standard CIE 1931.
  Obtain the conversion coefficients for colour to grey level starting from both measurements.

Figure 2:
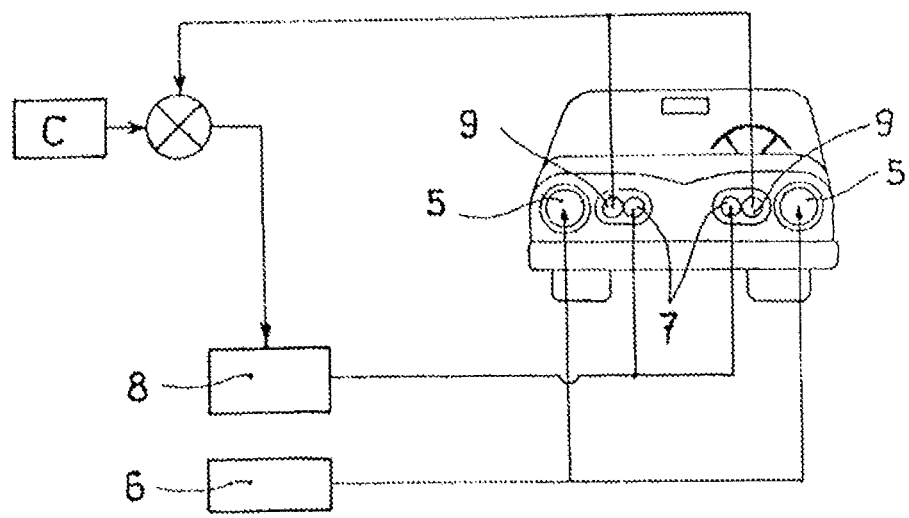
FIG. 2 shows the front of the above vehicle with the additional and base illumination devices.

The vehicle has two illumination systems, one which corresponds to the base illumination and the other which corresponds to the additional illumination. These two systems have to be adapted in order to permit a reliable measurement. See FIG. 2.

Base Illumination Device

In a preferred embodiment the base illumination (5) consists of the dipped lights of the vehicle, powered by the battery, whose voltage oscillates depending on its state of charge, its degree of aging, etc. Given that the illumination provided by these lights is directly related to the battery voltage, a stabilizer (6) needs to be inserted to compensate for the oscillations in that voltage.

Additional Illumination Device

In a preferred embodiment, the additional illumination (7) consists of the lamps external to the vehicle, which have to meet the following requisites:
  They must provide a constant level of illumination during the data gathering, independently of oscillations in the supply voltage, of the temperature of the bulbs of the external lamps, and of the wear undergone by those lamps with time.
  They have to provide a known level of illumination at each moment.
  The level of illumination has to be able to be adjustable for each specific period of data gathering.

On account of all this, an adjustment control system (8) is needed for the additional illumination in a closed loop that can take on these responsibilities. Basically, the functioning of this system can be summarized as:
  It measures the illumination by means of a sensor (9).
  It compares it with a desired level C, modifiable by the operator.
  It takes the decisions in the various control elements.

The map of intensity of the light provided by the additional lamps is known and controlled. Their light intensity is adjusted in such a way that avoids disturbing other circulating vehicles, preventing dangerous situations from arising that can be created by the other patents commented on above.

The additional lamps have to have a short response time. This can be achieved by means of lamps that are sufficiently fast (for example, based on LEDs) or with mechanical shutter systems that permit a sudden and controlled variation in the illumination that its provided.

The level of intensity of the illumination provided by the lamps has to be controlled and its geometric distribution has to be known.

The system described in the present embodiment permits data gathering to be done in movement along the road. In order to avoid disturbing other users travelling on the same road, it is necessary to follow the instructions regarding the design of lamps and maximum illumination levels for each emitter-observer angle that can be admissible, such as for example those defined in Regulation No 8 of the United Nations Economic Commission for Europe.

Image and Data Recording and Treatment System

The system comprises:
A digital storage device.
A device that applies some transformation equations enabling the luminance of each pixel to be obtained starting from its characteristic values (grey scale).

Positioning System

The system comprises:
A geo-referenced positioning device (GPS) and its corresponding antenna.
An information recording device.

Synchronism System

The system comprises a local positioning device (via the vehicle's milometer) which provides the distance travelled, and a device that generates certain events as a function of that distance travelled. The synchronism system allows adjustment of the distance from the start to when the images are captured and the delay time between each of them.

The synchronism system has to be such that permits adjustment of the on and off times of the lamps with sufficient precision for eliminating the subcyclic effects of public lighting. If f is the frequency of the grid (normally 50 Hz in Europe) the subcyclic effects have a duration of $1/(2*n*f)$ n= 1 ... N. On the other hand, given that the described device is capable of capturing images while moving, the duration of the time for capturing each image will be sufficiently small so as not to alter the size of the objects appearing in them and it will also be a multiple of the subcyclic frequencies. The interval of time between capturing two successive images of the same sign with variation in the illumination will be;

$$\Delta t = p/(2*n*f)$$

with n=1 ... N and p=1 ... P.

In this way, as "n" and "p" are whole numbers, the moment of capturing each image will occur at the same point of the wave of the supply voltage from the electric grid, thus minimizing the differences in the uncontrolled ambient illumination.

The general operating procedure is as follows. A vehicle fitted with the devices and systems described above can circulate on the road and record different sequences of images of various signs situated along that road. With a view to a better understanding vertical signs will, for example, be used, though the procedure of the present invention is valid for any kind of sign that is the object of study.

As the vehicle approaches the sign (11), the sign will be seen to become displaced in the image and its size will increase until it disappears from the field visible to the camera.

The method that allows the effects of external illumination, such as public lighting (10) for example, to be cancelled out consists of capturing images with different illumination levels, by a combination of base illumination (5) and the additional illumination (7) of the vehicle, obtaining the value of the differential luminance, which cancels out the effect of the ambient illumination as well as the base illumination of the vehicle.

Figure 3:
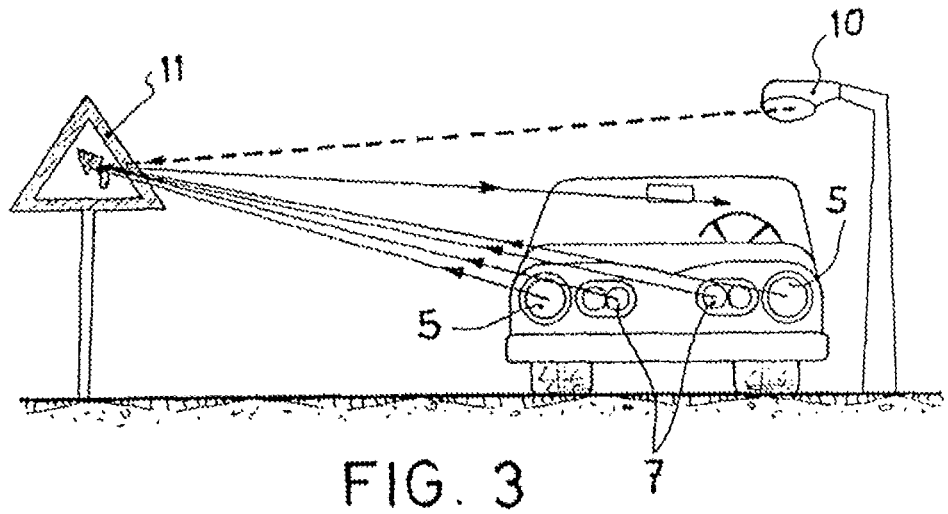
Figure 4:
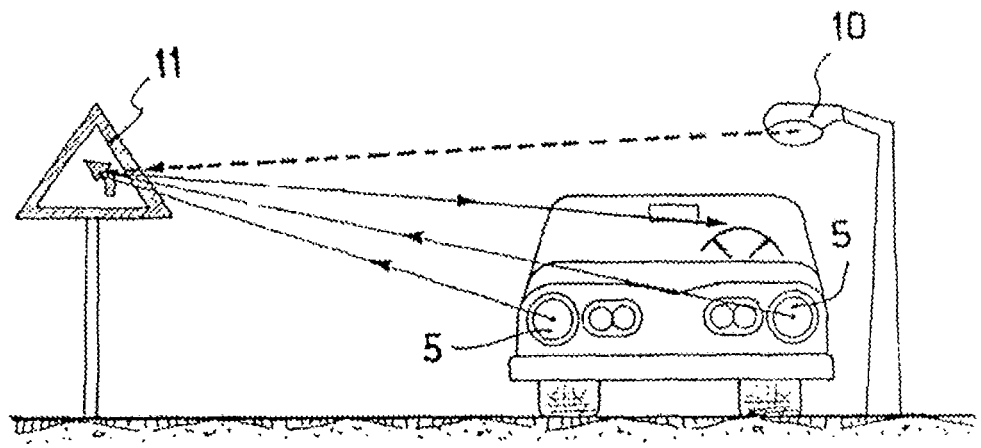

As can be seen in FIG. 3, first of all the images are captured with the base illumination (5) and the additional illumination (7) switched on. Then, with an interval of time determined by the synchronism device, the additional illumination (7) is switched off or hidden in order to obtain the second image as can be seen in FIG. 4.

Figure 5:
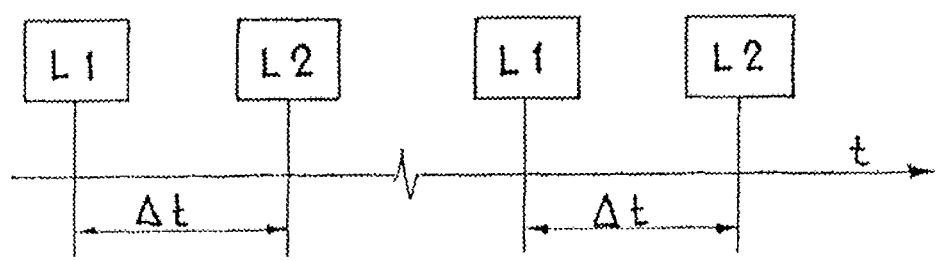
FIG. 5 shows, schematically in time, the determination of the luminance of two traffic signs.

The synchronism system establishes the instants of time in which the two images are captured corresponding to two illumination levels L1 and L2. See FIG. 5.

Finally, the location data is stored, along with the time of the synchronism system.

Once the data has been downloaded, an automatic computer programme processes the images where the vertical signs (11) appear and it extracts the region corresponding to that sign. Another automatic procedure calculates the luminance level on the basis of a grey scale. Finally, the differential luminance is obtained from L1 and L2.

The relation with the positioning system allows the relative position of the image and the sign on the road to be calculated.

It will be evident to an expert in the subject that, without departing from the essence of the invention, there is a series of modifications and variants that can be made allowing it to be adapted to the desired operating conditions. So, the additional illumination system has been described as an external light incorporated into the vehicle, but it could be included among the vehicle's own lamps with suitable control. No details have been given of those processes and devices which, being conventional, will be more than familiar to the expert in the subject.

The invention claimed is:

1. A computer-implemented method for determining luminance of a traffic sign, comprising the steps of:
    a) obtaining a first image using a first illumination level at a first point in time, the first illumination level being based on a first base illumination and a first ambient illumination;
    b) obtaining a second image using a second illumination level at a second point in time, the second illumination level being based on a second base illumination, a second ambient illumination and an additional illumination, the second illumination level being different from the first illumination level, a difference between the first point in time and the second point in time being an interval of time corresponding to a frequency of an electric grid such that the first image and the second image are obtained at a same point of a sine wave of a supply voltage from the electric grid;
    c) extracting a first array of pixels in the first image, the first array of pixels being representative of the traffic sign;
    d) extracting a second array of pixels in the second image, the second array of pixels being representative of the traffic sign;
    e) calculating a first luminance value of the traffic sign using the first array of pixels, the first luminance value being based on the first base illumination and the first ambient illumination;
    f) calculating a second luminance value of the traffic sign using the second array of pixels, the second luminance value being based on the second base illumination, the second ambient illumination and the additional illumination; and g) calculating a luminance difference value of the traffic sign corresponding to a difference between the first luminance value and the second luminance value.

2. The computer-implemented method of claim 1, wherein a camera is used to perform steps a) and b).

3. The computer-implemented method of claim 2, wherein the camera is coupled to a vehicle.

4. The computer-implemented method of claim 1, wherein a processor is used to perform steps c) through g).

5. The computer-implemented method of claim 4, wherein the processor is coupled to a vehicle.

6. The computer-implemented method of claim 1, wherein the first image includes a third array of pixels and wherein the second image includes a fourth array of pixels, the third array of pixels and the fourth array of pixels each corresponding to a second traffic sign.

7. The computer-implemented method of claim 1, further comprising:
emitting, via a stabilized base illumination light source, light corresponding to the first base illumination and the second base illumination.

8. The computer-implemented method of claim 7, further comprising:
stabilizing light to be emitted by the stabilized base illumination light source to compensate for oscillations in power supplied to the stabilized base illumination light source.

9. The computer-implemented method of claim 8, wherein the stabilized base illumination light source is coupled to a vehicle.

10. The computer-implemented method of claim 1, further comprising:
emitting, via an additional illumination light source, light corresponding to the additional illumination; and
stabilizing light to be emitted from the additional illumination light source to compensate for oscillations in power supplied to the additional illumination light source.

11. The computer-implemented method of claim 1, further comprising: establishing the first point in time when the first image is obtained and establishing the second point in time when the second image is obtained.

12. The computer-implemented method of claim 1, wherein calculating a luminance difference value further comprises:
cancelling out the first base illumination with the second base illumination; and
cancelling out the first ambient illumination with the second ambient illumination.

13. The computer-implemented method of claim 1, wherein the luminance difference value is a function of the additional illumination.

14. The computer-implemented method of claim 13, wherein the first base illumination is equal to the second base illumination and the first ambient illumination is substantially equal to the second ambient illumination.

15. A system for determining luminance of a traffic sign, comprising:
a camera configured to:
a) obtain a first image using a first illumination level at a first point in time, the first illumination level being based on a first base illumination and a first ambient illumination;
b) obtain a second image using a second illumination level at a second point in time, the second illumination level being based on a second base illumination, a second ambient illumination and an additional illumination, the second illumination level being different from the first illumination level, a difference between the first point in time and the second point in time being an interval of time corresponding to a frequency of an electric grid such that the first image and the second image are obtained at a same point of a sine wave of a supply voltage from the electric grid; and
a processor configured to:
c) extract a first array of pixels in the first image, the first array of pixels being representative of the traffic sign;
d) extract a second array of pixels in the second image, the second array of pixels being representative of the traffic sign;
e) calculate a first luminance value of the traffic sign using the first array of pixels, the first luminance value being based on the first base illumination and the first ambient illumination;
f) calculate a second luminance value of the traffic sign using the second array of pixels, the second luminance value being based on the second base illumination, the second ambient illumination and the additional illumination; and
g) calculate a luminance difference value of the traffic sign corresponding to a difference between the first luminance value and the second luminance value.

16. The system of claim 15, wherein the camera is coupled to a vehicle.

17. The system of claim 15, wherein the processor is coupled to a vehicle.

18. The system of claim 15, wherein the first image includes a third array of pixels and wherein the second image includes a fourth array of pixels, the third array of pixels and the fourth array of pixels each corresponding to a second traffic sign.

19. The system of claim 15, further comprising: a stabilized base illumination light source configured to emit light i) corresponding to the first base illumination included in the first illumination level and ii) corresponding to the second base illumination included in the second illumination level, wherein the first base illumination is equal to the second base illumination.

20. The system of claim 19, further comprising: a stabilizer device configured to stabilize light to be emitted from the stabilized base illumination light source to compensate for oscillations in power supplied to the stabilized base illumination light source.

21. The system of claim 20, wherein the stabilized base illumination light source is coupled to a vehicle.

22. The system of claim 15, further comprising: an additional illumination light source configured to emit light corresponding to the additional illumination; and a stabilizer device configured to stabilize light to be emitted from the additional illumination light source to compensate for oscillations in power supplied to the additional illumination light source.

23. The system of claim 15, further comprising: a synchronization system coupled to the camera, the synchronization system being configured to establish the first point in time when the first image is obtained and the second point of time when the second image is obtained.

24. The system of claim 15, wherein the first ambient illumination is substantially equal to the second ambient illumination.

25. A system for calculating a luminance of a traffic sign, comprising:
a camera configured to:
(i) obtain a first image of the traffic sign at a first point in time and (ii) obtain a second image of the traffic sign at a second point in time, a difference between the first point in time and the second point in time being an interval of time, the interval of time corresponding to a frequency of an electric grid such that the first image and the second image are obtained at a same point of a sine wave of a supply voltage from the electric grid;

a processor configured to:
   i) extract a first array of pixels in the first image, the first array of pixels being representative of the traffic sign;
   ii) extract a second array of pixels in the second image, the second array of pixels being representative of the traffic sign;
   iii) calculate a first luminance value of the traffic sign represented by a first array of pixels in the first image;
   iv) calculate a second luminance value of the traffic sign represented by a second array of pixels in the second image, the second luminance value being different from the first luminance value; and
   (v) calculate a luminance difference value corresponding to a difference between the first luminance value and the second luminance value.

26. The system according to claim 25, wherein the first image includes a first illumination level based on a first ambient illumination and the second image includes a second illumination level based on a second ambient illumination and an additional illumination, the first ambient illumination being substantially equal to the second ambient illumination.

27. The system of claim 26, wherein the first illumination level is based on a first base illumination and the second illumination level is based on a second base illumination, the first base illumination being equal to the second base illumination.

28. The system of claim 27, further comprising: a stabilized base illumination light source configured to emit light corresponding to i) the first base illumination and ii) the second base illumination.

29. The system of claim 28, wherein the stabilized base illumination light source is coupled to a vehicle.

30. The system of claim 28, further comprising: a stabilizer device configured to stabilize light to be emitted from the stabilized base illumination light source to compensate for oscillations in power supplied to the stabilized base illumination light source.

31. The system of claim 26, further comprising:
an additional illumination light source configured to emit light corresponding to the additional illumination; and
a stabilizer device configured to stabilize light to be emitted from the additional illumination light source to compensate for oscillations in power supplied to the additional illumination light source.

32. The system of claim 25, wherein a synchronization system is coupled to the camera, the synchronization system being configured to establish the first point in time when the first image is obtained and the second point of time when the second image is obtained.

33. The system of claim 25, wherein the camera is coupled to a vehicle.

34. The system of claim 25, wherein the processor is coupled to a vehicle.

35. The system of claim 25, wherein the first image includes a third array of pixels and wherein the second image includes a fourth array of pixels, the third array of pixels and the fourth array of pixels each corresponding to a second traffic sign.

36. A computer-implemented method for calculating a luminance of a traffic sign, comprising:
a) obtaining a first image of the traffic sign at a first point in time;
b) obtaining a second image of the traffic sign at a second point in time, a difference between the first point in time and the second point in time being an interval of time, the interval of time corresponding to a frequency of an electric grid such that the first image and the second image are obtained at a same point of a sine wave of a supply voltage from the electric grid;
c) extracting a first array of pixels in the first image, the first array of pixels being representative of the traffic sign;
d) extracting a second array of pixels in the second image, the second array of pixels being representative of the traffic sign;
e) calculating a first luminance value of the traffic sign represented by a first array of pixels in the first image;
f) calculating a second luminance value of the traffic sign represented by a second array of pixels in the second image, the second luminance value being different from the first luminance value; and
g) calculating a luminance difference value of the traffic sign corresponding to a difference between the first luminance value and the second luminance value.

37. The computer-implemented method of claim 36, wherein a camera is used to perform steps a) and b).

38. The computer-implemented method of claim 37, wherein the camera is coupled to a vehicle.

39. The computer-implemented method of claim 36, wherein a processor is used to perform steps c) through e).

40. The computer-implemented method of claim 39, wherein the processor is coupled to a vehicle.

41. The computer-implemented method of claim 36, wherein the first image includes a third array of pixels and wherein the second image includes a fourth array of pixels, the third array of pixels and the fourth array of pixels each corresponding to a second traffic sign.

42. The computer-implemented method of claim 36, wherein the first image includes a first illumination level based on a first ambient illumination and the second image includes a second illumination level based on a second ambient illumination and an additional illumination, the first ambient illumination being substantially equal to the second ambient illumination.

43. The computer-implemented method of claim 42, wherein the first illumination level is based on a first base illumination and wherein the second illumination level is based on a second base illumination, the first base illumination being equal to the second base illumination.

44. The computer-implemented method of claim 43, further comprising:
emitting, via a stabilized base illumination light source, light corresponding to the first base illumination and the second base illumination; and
stabilizing light to be emitted from the stabilized base illumination light source to compensate for oscillations in power supplied to the stabilized base illumination light source.

45. The computer-implemented method of claim 44, wherein the stabilized base illumination light source is coupled to a vehicle.

46. The computer-implemented method of claim 42, further comprising:
emitting, via an additional illumination light source, light corresponding to the additional illumination; and
stabilizing light to be emitted from the additional illumination light source to compensate for oscillations in power supplied to the additional illumination light source.

47. The computer-implemented method of claim 36, further comprising: establishing the first point in time when the first image is obtained and establishing the second point in time when the second image is obtained.

* * * * *